United States Patent [19]
Phan et al.

[11] Patent Number: 5,129,910
[45] Date of Patent: Jul. 14, 1992

[54] STONE EXPULSION STENT

[75] Inventors: Cu N. Phan; Marshall L. Stoller, both of San Francisco, Calif.

[73] Assignee: The Regents of the University of California, Oakland, Calif.

[21] Appl. No.: 736,187

[22] Filed: Jul. 26, 1991

[51] Int. Cl.⁵ .................. A61M 1/00; A61M 25/00
[52] U.S. Cl. ................................ 606/127; 606/108; 604/93; 604/264
[58] Field of Search ............... 606/108, 127, 128, 159, 606/191, 193, 194; 604/93, 264

[56] References Cited

U.S. PATENT DOCUMENTS

| | | | |
|---|---|---|---|
| 2,756,752 | 7/1956 | Scherlis | 606/127 |
| 4,030,503 | 6/1977 | Clark, III | 606/159 |
| 4,243,040 | 1/1981 | Beecher . | |
| 4,295,464 | 10/1981 | Shihata . | |
| 4,469,100 | 9/1984 | Hardwick . | |
| 4,515,593 | 5/1985 | Norton | 604/265 |
| 4,601,713 | 7/1986 | Fuqua . | |
| 4,657,020 | 4/1987 | Lipton | 606/127 |
| 4,690,672 | 9/1987 | Veltrup . | |
| 4,706,671 | 11/1987 | Weinrib | 606/159 |
| 4,762,130 | 8/1988 | Fogarty et al. | 606/159 |
| 4,790,812 | 12/1988 | Hawkins, Jr. et al. . | |
| 4,794,928 | 1/1989 | Kletschka | 606/159 |
| 4,883,458 | 11/1989 | Shiber . | |
| 5,011,489 | 4/1991 | Salem | 606/159 |

FOREIGN PATENT DOCUMENTS

| | | | |
|---|---|---|---|
| 1069823 | 11/1959 | Fed. Rep. of Germany | 606/127 |
| 2847633 | 5/1979 | Fed. Rep. of Germany | 606/127 |
| 2923105 | 12/1980 | Fed. Rep. of Germany | 606/127 |
| 8200592 | 3/1982 | PCT Int'l Appl. | 606/159 |
| 8300997 | 3/1983 | PCT Int'l Appl. | 606/159 |
| 0002523 | 3/1990 | PCT Int'l Appl. | 606/127 |
| 0584856 | 12/1977 | U.S.S.R. | 606/159 |
| 1200904 | 12/1985 | U.S.S.R. | 606/127 |

Primary Examiner—Stephen C. Pellegrino
Assistant Examiner—Glenn K. Dawson
Attorney, Agent, or Firm—Townsend and Townsend

[57] ABSTRACT

A stent of the present invention includes a tubular body having a helical-like ridge along at least a portion of its outer wall for expelling masses within a body passage. The helical-like ridge includes a smooth, convex superior surface having a beveled central portion, and a concave inferior surface.

26 Claims, 7 Drawing Sheets

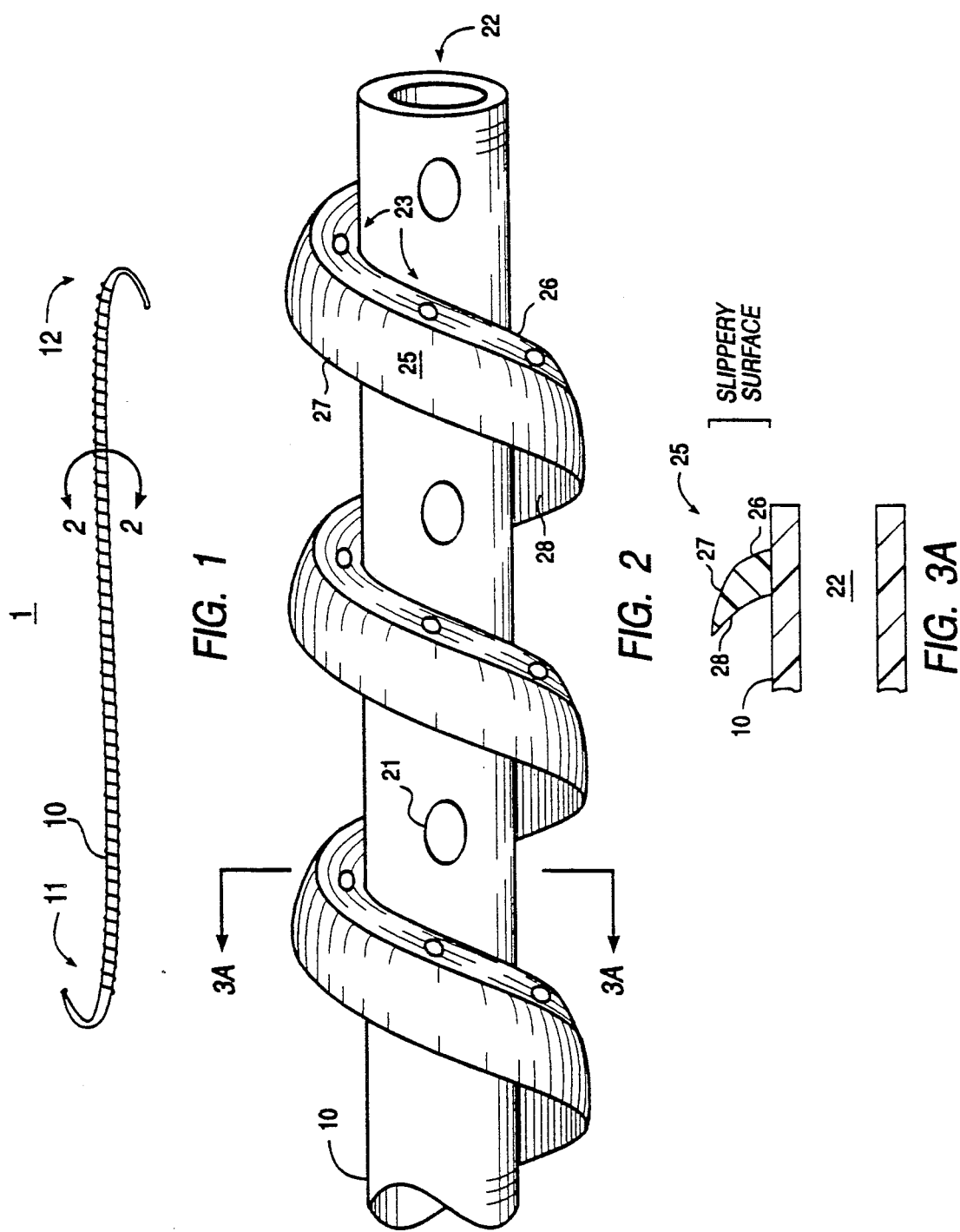

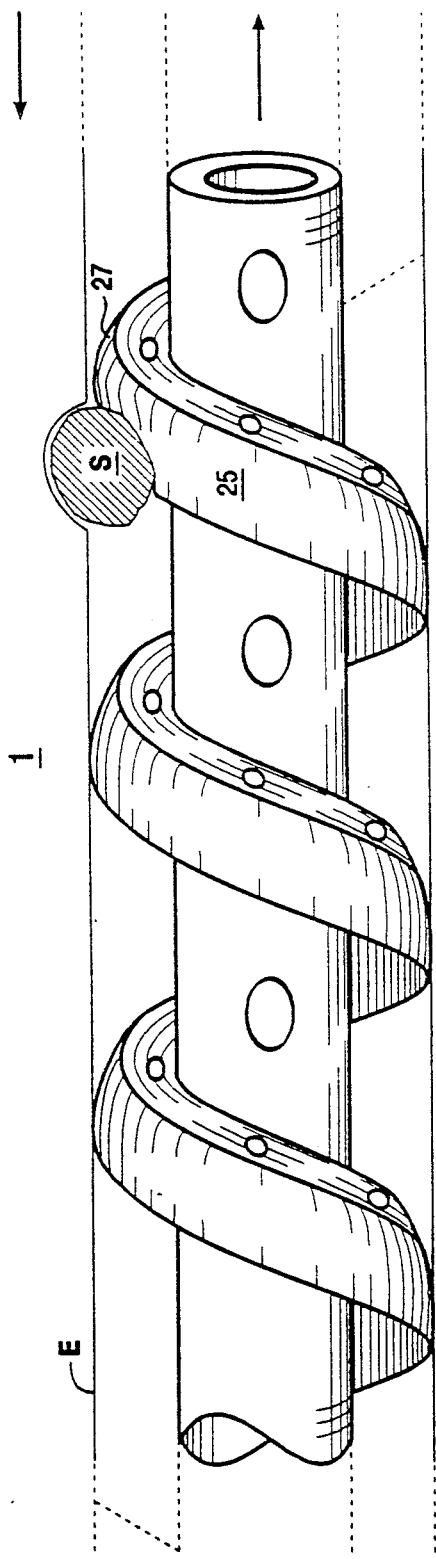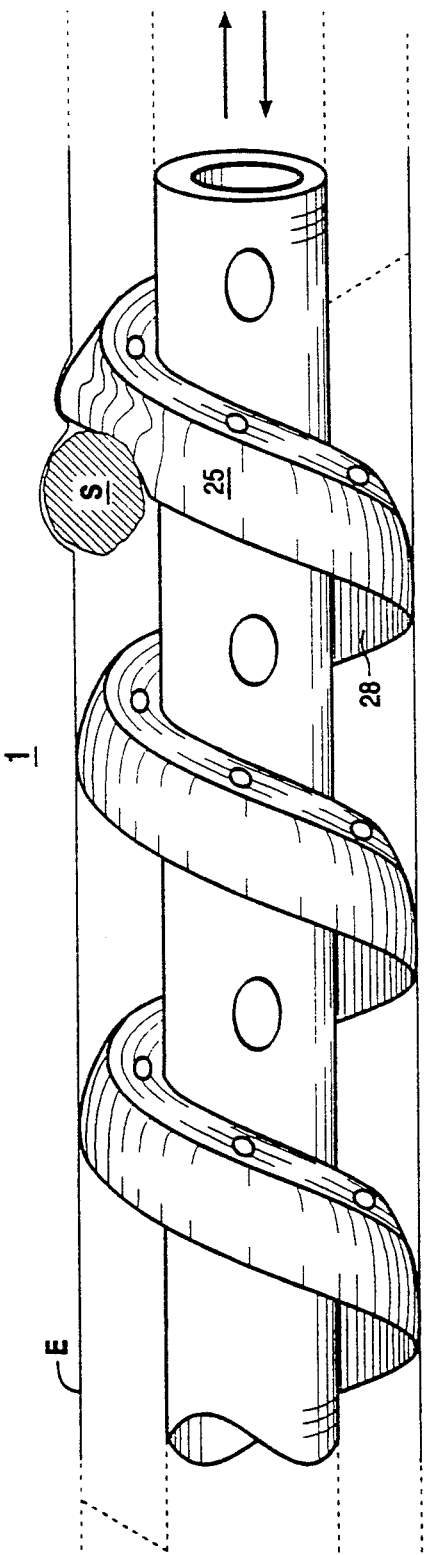

STONE EXPULSION STENT

BACKGROUND OF THE INVENTION

1. Field of Use

The present invention relates generally to the removal of solid masses from body passages. More particularly, the invention relates to a stent for expelling stones and their fragments from luminal passages of the human body.

Lithiasis is a common human ailment characterized by calculi or "stones" formed within a passage of the human body. While stones have been documented in just about every passage within the body, kidney stones (nephrolithiasis) and gallstones (cholelithiasis) remain the most common. Regardless of location, however, a stone is typically an extremely hard and unyielding mass which blocks the passage in which it presents.

Kidney stones typify the pathogenesis of stones. These stones, which include calcium or other particulate matter, form hard, irregular masses within the renal calyces or pelvis. Responding to normal urinary flow and pressure, these stones attempt to pass from the kidney, through the ureter, into the urinary bladder, and eventually out through the urethra. Usually, however, the stones cause blockage of the urinary tract producing renal colic with accompanying severe pain.

Most stones will eventually pass. To facilitate the process, though, lithiasis patients often receive intravenous hydration (leading to increased urine output) and parenteral analgesics. As a result of regular peristaltic contractions of ureteral muscles, a stone is usually pushed or flushed outward.

The process may become complicated however. As the stone rubs back and forth (under the influence of peristaltic waves), the delicate lining (endothelium) of the ureter is disrupted. Accompanying swelling or edema effectively reduces the size of the ureteral lumen and impedes or even prevents the passage of the stone. In addition, stones which are relatively large (greater than 0.5 cm) or irregularly shaped frequently become trapped.

Stones which do not pass spontaneously require further intervention. In the past, surgical or other invasive intervention was commonly employed for such stones. Modern treatment, however, favors less invasive or non-invasive modalities. Extracorporeal shockwave lithotripsy, for example, is a non-invasive treatment where sonic or shockwaves are employed to crush calculi into smaller fragments which may then be passed. Other known forms of lithotripsy include ultrasonic, electrohydralic, and laser lithotripsy.

A major impediment to the widespread use of these and other fragmenting techniques has been the elimination of stone fragments from the urinary tract. One approach to this problem has been the use of stents or small catheters to facilitate the passage of fragments while maintaining the patency of the lumen so that urine may pass. In typical use, a stent is placed by cystoscopic technique within the ureter of interest. Once in position, the stent facilitates the passage of the stone fragments by providing a larger passage and, hence, one with less resistance.

The operation of current stents is far from perfect however. Most stone fragments tend to aggregate along side of a stent instead of going through the stent. The fragments, which are trapped between the stent and the endothelium, constantly roll back and forth with movement, including peristalsis, of the urinary tract. This Sisyphean motion further disrupts the delicate endothelial lining of the ureter and leads to increased edema. In fact, the back-and-forth fashion in which conventional stents move stones may actually impede caudal passage of stone fragments.

Thus, it is desirable to provide improved apparatus and methods for the removal of masses (e.g., stones and stone fragments) from body passages, such as the urinary and biliary tracts. The stent should be suitable for introduction to a desired location within a passage, preferably utilizing conventional placement techniques (e.g., cystoscopy, endoscopy, and the like). In addition to maintaining the patency of the passage, the stent should also actively facilitate the expulsion of masses outward from the passage. Furthermore, the stent should minimize trauma to the surrounding tissue and should be suitable for placement for extended periods of time. The present invention fulfills this and other needs.

2. Description of the Background Art

U.S. Pat. No. 4,295,464 describes a ureteric stone extractor comprising a relatively large outer dilator catheter with an inner dislodger catheter slideably disposed within. The inner catheter is provided with a balloon which is inflated once the inner catheter is positioned beyond the arrested stone. Nylon strings positioned along longitudinal axes of the balloon are used to entrap the stone and dislodge it from the ureteral wall.

U.S. Pat. No. 4,690,672 describes a catheter having a mouth in communication with a suction duct and a tongue projecting beyond the mouth; the tongue includes a nozzle aperture for training a jet of fluid into the mouth.

U.S. Pat. No. 4,469,100 describes a double lumen catheter for removing foreign bodies such as a ureteral stone from a body passage. The catheter includes a suction lumen which opens at a distal end and a pressure applying lumen which is open to the interior of the balloon. After placement, the catheter is slowly withdrawn causing intussusception of the distal end of the balloon, thereby surrounding the stone.

U.S. Pat. No. 4,243,040 describes a stone extracting device having an inflatable sleeve attached at the distal end of a tube. When the sleeve is inflated, the distal end of the sleeve is turned inside out and forms a soft annular flaring for engaging a stone. The stone may be captured by suction applied through an inner tube.

U.S. Pat. No. 4,790,812 describes a catheter which includes a parachute basket. A target object is fragmented by a cutting tip at the distal end of the catheter; the parachute basket is deployed downstream of the target object for capturing any fragments which are not aspirated into the catheter lumen.

U.S. Pat. No. 4,883,458 describes an arthrectomy catheter and guidewire for removing an obstruction from within a vessel; the guidewire may include a distal barrier in the form of an umbrella for countering the distal movement of surrounding obstruction material.

U.S. Pat. No. 4,601,713 describes a variable diameter catheter which may be used as a "kidney tube" for excavating stones.

The disclosures of each of the foregoing patents are hereby incorporated by reference.

SUMMARY OF THE INVENTION

The present invention comprises apparatus, stents, and methods for the removal of masses, particularly stones and their fragments, from the passages of a human body. The stent of the present invention includes an elongate, flexible tubular body with proximal and distal ends. The body may include one or more tubular members having one or more lumens. In a preferred embodiment, the body includes a single tubular member having a central lumen extending from the proximal end to the distal end.

The stent also includes a spaced-apart barrier, disposed along at least a portion of the tubular body, for urging masses out of the body passage. The barrier may be in the form of one or more ridges, edges, fins, flippers, flutes, and the like.

In a preferred embodiment, the barrier is a continuous helical-like ridge having superior and inferior surfaces. The superior surface is generally convex in configuration and includes a bevel at its central portion. The inferior surface, on the other hand, defines a substantially concave surface.

Both the tubular body and the ridge may include passageways for permitting fluid flow. The passageways may be in the form of circular or oval sideholes, or the like. The passageways of the tubular body will typically be of sufficient width and configuration to accommodate small fragments and particulate matter, in addition to fluid flow.

Employing a ratcheting or staircase transport mechanism (or both), the stent expels the fragments from the ureter, and hence out of the passage. In particular, the fragments, in response to movement of and/or within the passage, slide over the convex surface of successive segments of the helical-like ridge; movement may include relative/differential motion due to respiratory motion or body movement, peristaltic contractions of the passage, fluid flow within the passage, and the like. Retrograde movement of fragments is prevented by the concave surface. Alternatively, fragments may slide down the bevel surface, which presents a smooth and continuous path out of the passage. The fragments may also be trapped by the stent, e.g., within the passageways, and expelled upon removal of the stent. In addition, small fragments may pass straight through the central lumen.

In a method of the present invention, a stone or calculus is fragmented using extracorporeal lithotripsy. Next, under conventional cystoscopic guidance techniques, the stent of the present invention is introduced into the ureter of interest. Employing any or all of the aforementioned mechanisms, stones and their fragments are expelled from the urinary tract. An alternative method is also described for expelling stones and their fragments from the biliary tract.

BRIEF DESCRIPTION OF THE DRAWINGS

FIG. 1 is a lateral view of a stent constructed in accordance with the principles of the present invention.

FIG. 2 is a lateral view of an enlarged portion of the stent taken along line 2—2 of FIG. 1.

FIG. 3A is an enlarged longitudinal section taken along line 3A—3A of FIG. 2.

FIGS. 4-7 illustrate a stone expulsion mechanism of the stent of the present invention.

DESCRIPTION OF A PREFERRED EMBODIMENT

Figure 3B:
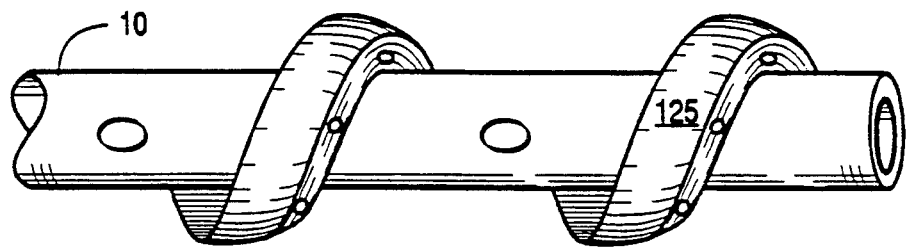
FIGS. 3B-3E illustrate alternative stent configurations.
Figure 3C:
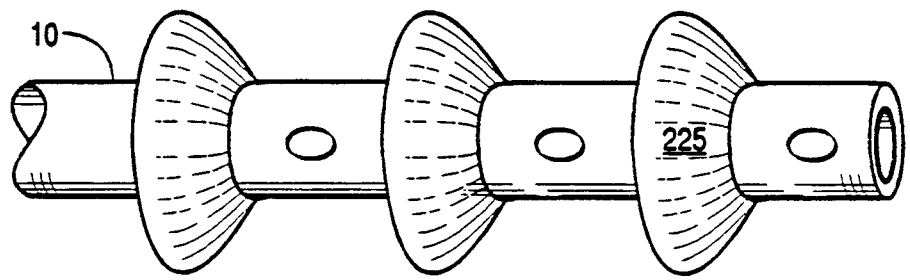

The present invention is useful for the removal of masses from a body passage. The present invention will find particular application in passages afflicted with hard, irregular masses, such as stones and stone fragments. Furthermore, the present invention is particularly useful for those passages which have a fluid flow and exhibit rhythmic contractions or movement, such as peristaltic activity.

The following discussion will focus on the treatment of stones and stone fragments within the urinary tract, including the kidneys, ureters, bladder, and/or urethra. The present invention, however, is not limited to such treatment and instead may be advantageously applied to other specific passages within the body, such as the biliary, salivary, and vascular passages.

The stent or catheter of the present invention comprises an elongate, flexible tubular body having proximal and distal ends. The length and diameter of the body vary depending on the site of its intended use. For urological applications, the stent will typically have a length in the range from about 20 to 30 cm; and a diameter in the range from about 4 to 9 French. The general configuration of the tubular body may also be adapted for site-specific use. When intended for placement within the urinary tract, for example, the tubular body will preferably have a "double-J" configuration.

The tubular body may be formed by extrusion of an organic polymer, such as nylon, polyurethane, polyvinyl chloride (PVC), or the like. Processes for forming stent bodies are known, and can be found in the patent, medical, and catheter literature.

The tubular body will include at least one lumen extending from the proximal end to the distal end for the passage of fluid (e.g., urine) therethrough. Additional lumens may be provided as required by the intended application. It may be desirable, for example, to provide suction and irrigation lumens as taught by U.S. Pat. No. 4,690,672.

In a preferred embodiment, the tubular body is constructed to prevent occlusion. In an exemplary embodiment, for example, the tubular body includes radial passageways such as a plurality of oval or circular side holes. Thus, at several locations along the tubular body, fluid communication exists between the body passage and the central lumen of the stent. As a result, fluid or gas within the body passage is able to flow to a lower pressure region (i.e., outward). An obstruction within the central lumen itself will not impede the flow within the body passage as the flow is channeled around the obstruction. Similarly, an obstruction external to the stent (i.e., between the tubular body and an inner wall of the passage) will not obstruct flow, as the flow will be channeled into the central lumen via the side holes, and then out through the distal end of the tube (or a distal side hole).

Those skilled in the art will appreciate other configurations for the radial passageways. The passageways may include, for example, fenestrations, permeable membranes, screens, vents, slits, and the like.

The stent of the present invention includes a spaced-apart barrier for urging masses, such as stones and stone fragments, outward from the passage in response to natural motion of and/or within the passage. The kidneys, for example, are not fixed. Instead, they move with respiration or flexion/extension of the back. As a result, a stent internalized or placed within a ureter will move at a rate and amplitude different than the surrounding ureteral endothelium or urothelium. Furthermore, other movements, including peristaltic contractions and urine flow, are present. Gravity may also contribute to stone movement.

To harness this differential motion, the barrier of the stent may be in the form of one or more ridges, edges, fins, flippers, flutes, and the like. In an exemplary embodiment, the stent includes a helical-like ridge disposed along at least a portion of the tubular body. In particular, the helical-like ridge forms a continuous spiral structure around at least a portion of the tubular body. Effectively, the stones and their fragments are actively moved or "ratcheted" in a caudal and unidirectional fashion.

In a preferred embodiment, the helical-like ridge is disposed along substantially the entire length of the stent and includes both superior and inferior surfaces. The superior surface or edge will typically define a substantially convex surface and face towards the flow within the body passage (e.g., in an efferent and caudal direction for a ureteral stent). To further facilitate the passage of masses, the superior surface may include a beveled portion, typically constructed centrally (i.e., at the junction of the superior surface of the helical-like ridge with the tubular body). The inferior surface, on the other hand, will typically define a substantially concave surface.

In this manner, a longitudinal section through one-half turn of the helical-like ridge resembles one-half of an umbrella, with the superior surface corresponding to the outer or top surface of the umbrella while the inferior surface corresponds to the inside or bottom surface of the umbrella. As a result of the differential motion between the overlying endothelium and the stent, stones and their fragments are allowed to slip over the superior surface (umbrella top) of the helical-like ridge. Once over the superior surface, however, the masses or objects are prevented from moving in a retrograde fashion by the concave inferior surface of the ridge (inside umbrella), as described further hereinbelow.

In a preferred embodiment, the helical-like ridge is a pliable structure with a smooth and hydrophilic surface. It may be formed from a variety of plastics, resins, or organic polymers, including thermoplastics, and may be the same as described hereinabove for the tubular body.

Like the tubular body, the helical-like ridge may include passageways for permitting flow. The passageways may be the same as or similar to the radial passageways of the tubular body. Generally though, the passageways of the helical-like ridge, being adapted mainly for fluid flow, will be smaller in width than those of the tubular body.

Referring now to FIGS. 1-3, an exemplary stent 1 constructed in accordance with the principles of the present invention will be described. The stent 1 comprises a tubular body 10 having a proximal end 12 and a distal end 11. The tubular body 10 may include one or more tubular members. In a preferred embodiment, body 10 comprises a single flexible tubular member having a central lumen 22 extending from the proximal (cephalad) end 12 to the distal (caudal) end 11. The tube 10 is constructed of a smooth, pliable material, such as nylon, polyurethane, urethane, polyethylene, polyvinyl chloride (PVC), or polyimide, thus allowing the tube to flex for easy placement within a body passage.

Those skilled in the art will appreciate certain modifications to the tube 10 which may be made within the scope of the present invention. The tube 10 may include, for example, a self-retaining configuration. When adapted for urological applications, tubular body 10 may include bends at each end so that it defines a double-J tube (as shown). The proximal J prevents the stent from migrating into the ureter; the distal J prevents migration upward into the ureter. Alternatively, tube 10 may be adapted to receive a retention suture, for example, by including an eyelet. In addition, tubular body 10 may include radiopaque markers, for example at its distal end 11, for location and identification of the stent 1. Distal end 11 may also be magnetized for identification and removal.

To permit fluid communication between the central lumen 22 and a region exterior to the stent 1, the tubular body 10 includes a plurality of passageways 21 in the form of oval side holes. Those skilled in the art will appreciate a variety of other configurations and structures which may function as the radial passageways 21. The passageways may include, for example, fenestrations, vents, membranes, screens, pores, and the like. Preferably, passageways 21 are sufficiently large to prevent occlusion with mucus, cellular or proteinaceous debris, particulate matter, and the like. In addition, passageways 21 may be sufficiently large to accommodate smaller masses, such as stone fragments, which may pass into the central lumen 22 for rapid removal from the body passage.

Stent 1 includes a barrier for transporting or urging masses out of a body passage. In the embodiment of stent 1, a helical-like ridge 25 is disposed along at least a portion of the stent. In particular, helical-like ridge 25 forms a continuous spiral structure which is secured to an outer wall of the tubular body 10.

With particular reference to FIG. 3A, helical-like ridge 25 includes two exterior surfaces: a superior surface 27 and an inferior surface 28. The surface 27 presents a substantially convex surface facing superior and lateral directions. Along a central portion (i.e., that which is closest to the tube 10), the superior surface 27 includes a beveled surface 26. On an opposing side, helical-like ridge 25 presents the inferior surface 28 which is substantially concave in configuration and faces inferior and central directions.

The helical-like ridge 25 is a pliable structure with smooth, hydrophilic exterior surfaces, and may be formed of the same or similar material as the stent. When positioned within a body passage, helical-like ridge 25 presents a slippery surface, i.e., one with a very low coefficient of friction. Thus masses, including irregularly shaped stones, are readily forced over the superior surface 27 of the ridge 25 during differential motion between the ureteral endothelium and the stent, resulting from peristaltic activity, fluid flow (e.g., urine), respiratory movement, flexion and extension of the back, and/or gravity.

Beveled surface 26 also presents a slippery, although somewhat flatter, surface. Bevel 26 permits masses (those which are not passing over the superior surface 27) to move outward in a helical-like fashion by sliding down a trough (formed by bevel 26, tube 10, and inferior surface 28), as if the mass were descending a spiral staircase. As shown, bevel 26 may include passageways 23, such as holes or the like, for permitting flow in an outward direction. Fluid flow through passageways 23 may serve to further urge masses outward (as described hereinbelow with reference to FIG. 8).

Figure 3D:
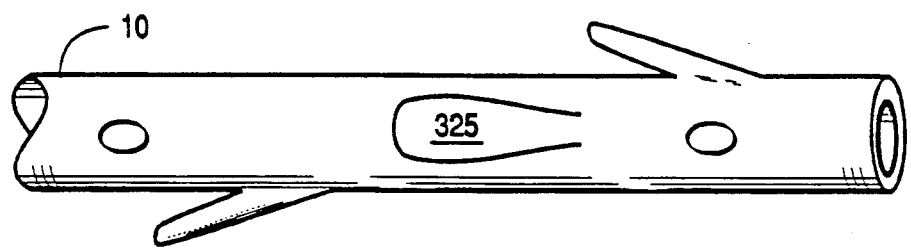
Figure 3E:
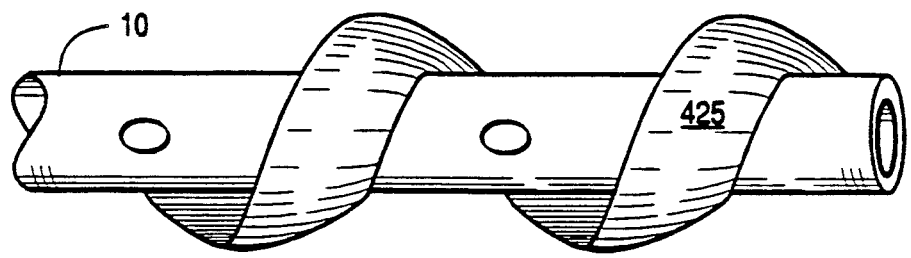

The barrier of the present invention may have a variety of other configurations, such as those shown in FIGS. 3B-E. In FIG. 3B, tube 10 includes a plurality of non-continuous helical-like ridges 125, and in FIG. 3C, the tube 10 includes a plurality of conical surfaces 225. In FIG. 3D the tube 10 includes a plurality of flippers 325. The size of the flippers may be reduced and their number increased, thereby creating a villus barrier, i.e., one with a plurality of finger-like projections. In FIG. 3E, tube 10 includes a continuous helical-like ridge 425 which is flatter and less tightly coiled than the previously described continuous helical-like ridge 25 (of FIG. 2). Thus, the barrier surface of the present invention includes any of the foregoing configurations, which limit movement of a mass substantially to a single net direction.

Figure 4:
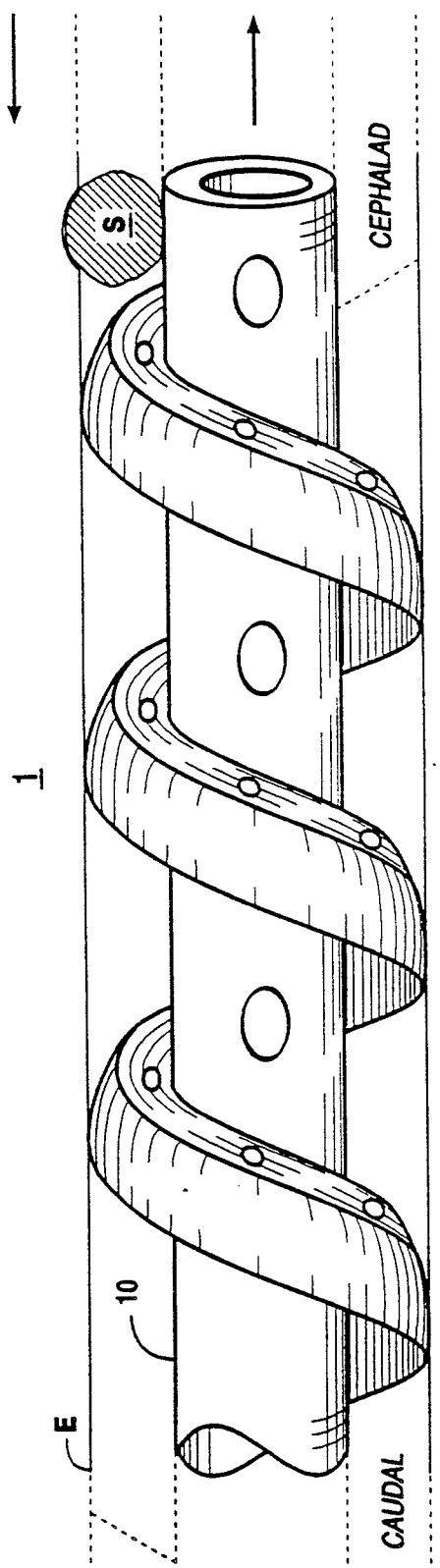

Referring now to FIGS. 4-7, a first mechanism for stone expulsion is illustrated for the stent 1. As shown in FIG. 4, a stone fragment S, which is interposed between the body 10 and the endothelium E of the ureter, approaches from the cephalad (i.e., from the kidney) direction.

Figure 5:
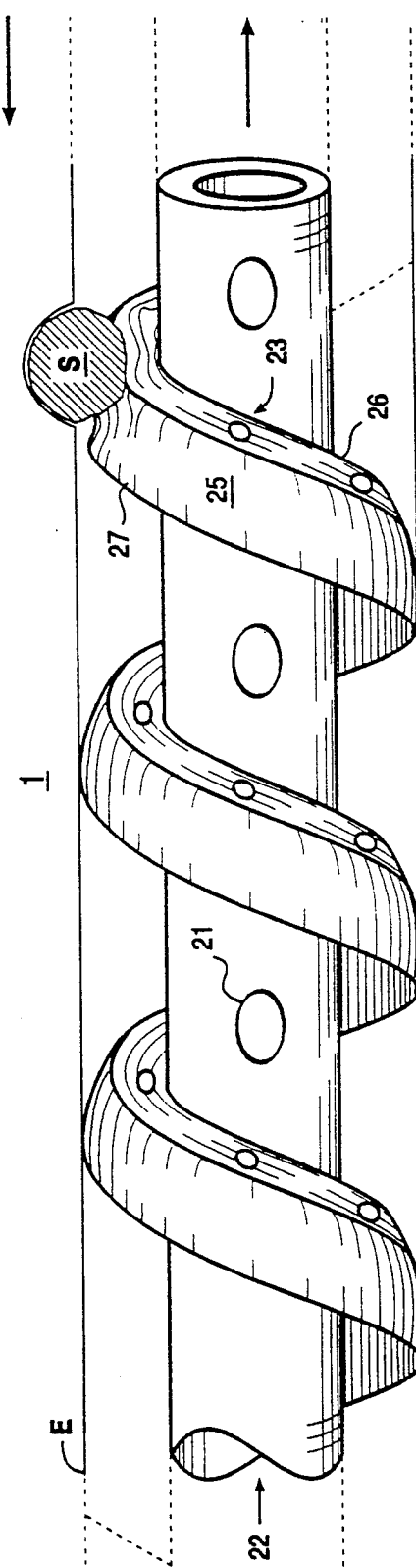

In FIG. 5, stone fragment s has moved in a caudal direction in response to relative motion of the ureter. Also moving with peristaltic contractions, the stent 1 may shift to and fro in a ratchet-like fashion (indicated by the arrows). As shown, fragment s has engaged the helical-like ridge 25. In particular, the stone fragment s has slid over the smooth beveled surface 26 onto the smooth superior surface 27. Throughout the process, fluid flow (e.g., urine) continues through the central lumen 22 as well as through passageways 23 and 21. In addition, if stone fragment S were small enough, it may pass through the central lumen 22 and/or the passageways 21.

In FIG. 6, stone fragment S has continued its antegrade movement (i.e., out of the passage) by traversing the smooth superior surface 27 of helical-like ridge 25. As shown in FIG. 7, however, the stone fragment s is unable to move retrograde. When stone fragment s attempts to move in a retrograde fashion (e.g., as a result of peristaltic activity), it is trapped by the concave surface 28 of helical-like ridge 25. All told, a mass may progress in only one direction, i.e., the antegrade or caudal direction, by traversing successive segments of the helical-like ridge, which resemble a series of umbrella-like surfaces.

Figure 8:
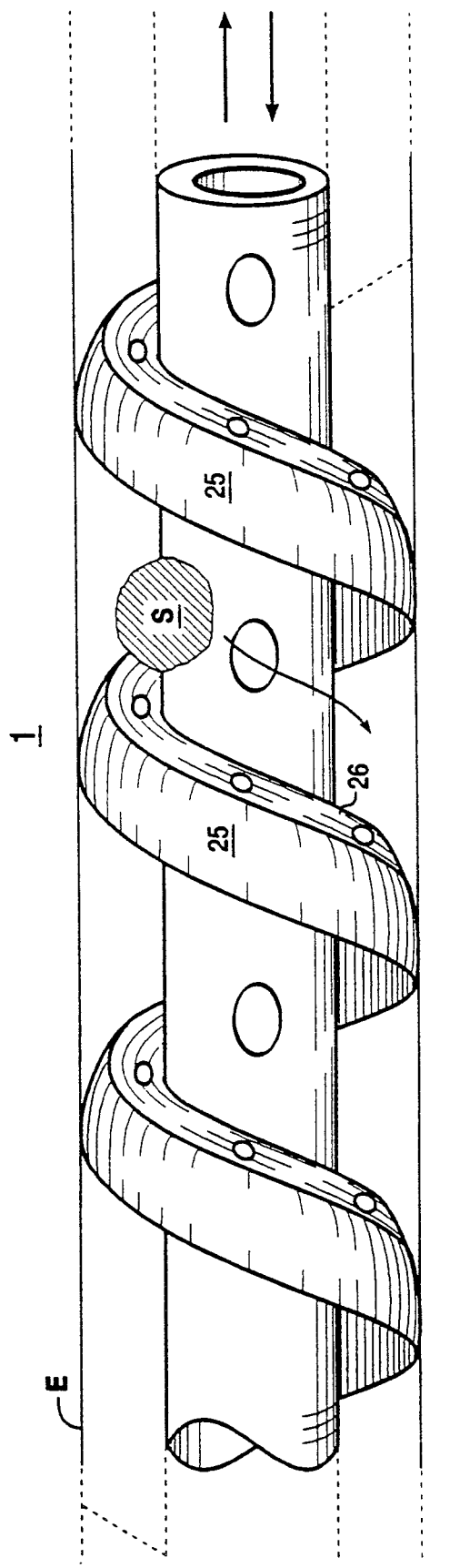
FIG. 8 illustrates an alternative stone expulsion mechanism of the stent of the present invention.

Referring now to FIG. 8, a second mechanism of mass expulsion is illustrated. In this case, stone fragment S lies between two segments of the helical-like ridge 25. In response to urine flow, which passes through passageways 23, the stone fragment s slides down the tubular body 10, guided by the smooth beveled surface 26; gravity may also aid this process. Thus, the second technique resembles an object descending a helical-like trough or spiral staircase.

As a third mechanism for stone removal, stones and their fragments may be trapped by the stent 1. For example, certain stones may be caught within the passageways or trapped between segments of the ridge 25. The expulsion of these masses is completed upon removal of the stent from a treated passage.

Those skilled in the art will appreciate that the actual mechanism for expelling a given stone or stone fragment may be the first technique, the second technique, the third technique, and/or any combination thereof. A stone fragment may, for example, initially traverse several segments of the helical-like ridge 25, then glide along the smooth beveled surface 26 in a spiral fashion, and finally enter the central lumen 22 (through the passageway 21) whereupon it is discharged with the urine flow.

Figure 9:
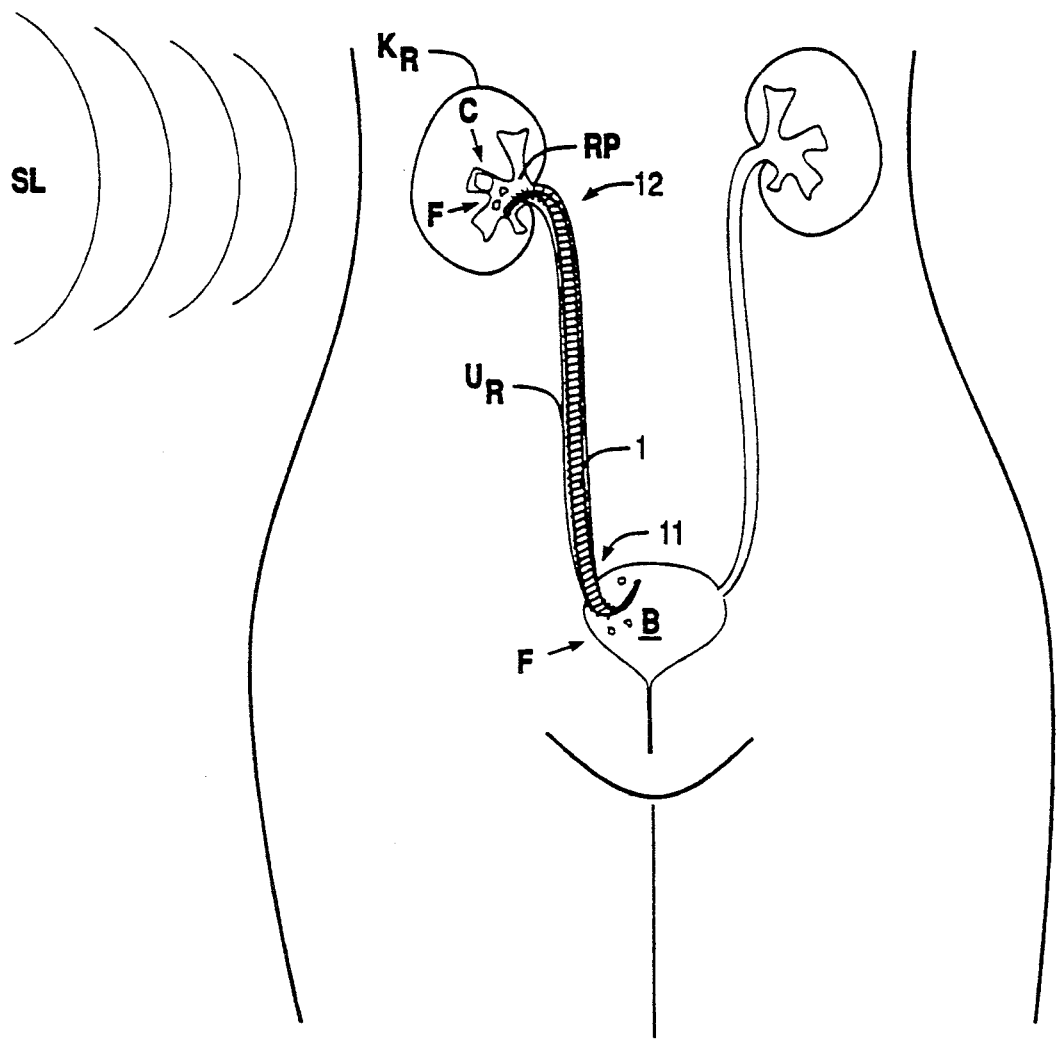
FIG. 9 illustrates a method of the present invention for removing masses from a urinary passage.

Referring now to FIG. 9, treatment of a calculus C in a patient's right kidney $K_R$ using the apparatus and method of the present invention will be described. After adequate preparation of the patient, the calculus C is crushed, for example, by using extracorporeal shockwave lithotripsy SL (or other fragmenting techniques).

Next, the stent 1 is placed into the right ureter $U_R$. In particular, under direct and/or fluoroscopic visualization using conventional cystoscopic techniques, the right ureter is cannulated with the stent before or after lithotripsy. The stent 1 is positioned so that the proximal J end 12 of the stent lies in the renal pelvis RP and the distal J end 11 lies within the urinary bladder B. The convex edge of the helical-like ridge faces towards the kidney $K_R$ (afferent and cephalad direction) and the concave edge faces towards the urinary bladder B (efferent and caudal direction).

After proper placement, stones and stone fragments F are actively expelled from the right ureter $U_R$ into the bladder B of the patient by the aforementioned ratcheting, staircase, and/or trapping mechanisms. After resolution of the stones and/or stone fragments, or after a desired period of treatment, the stent is removed and the procedure is terminated.

Figure 10A:
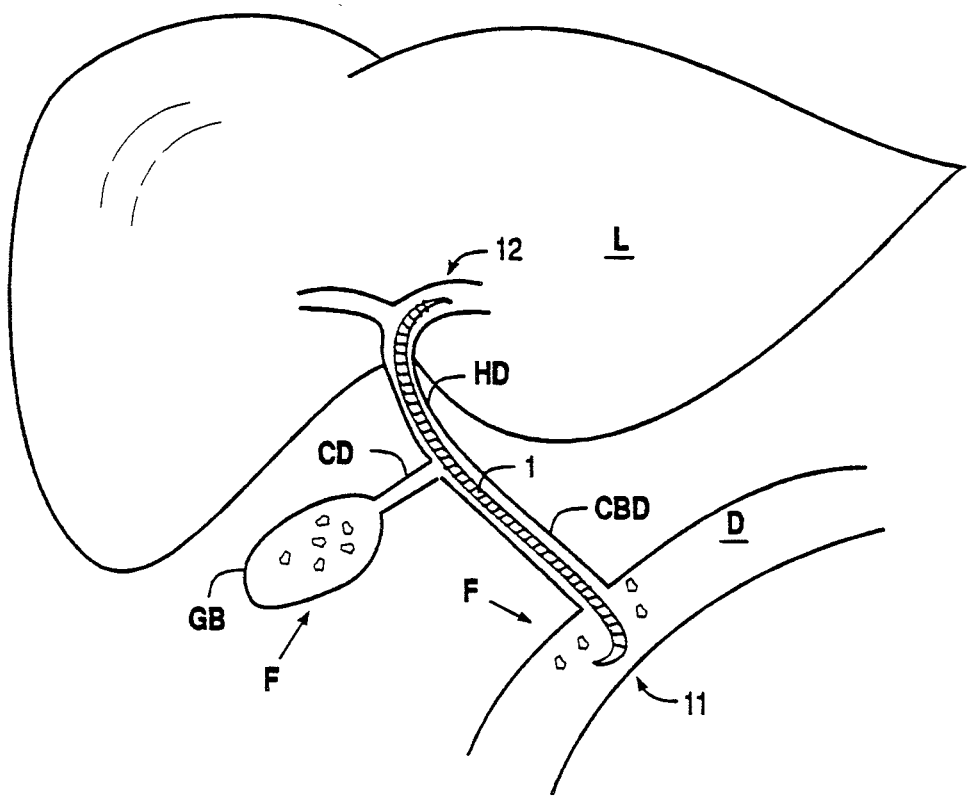
FIGS. 10A-B illustrate a method of the present invention for removing masses from a biliary passage.
Figure 10B:
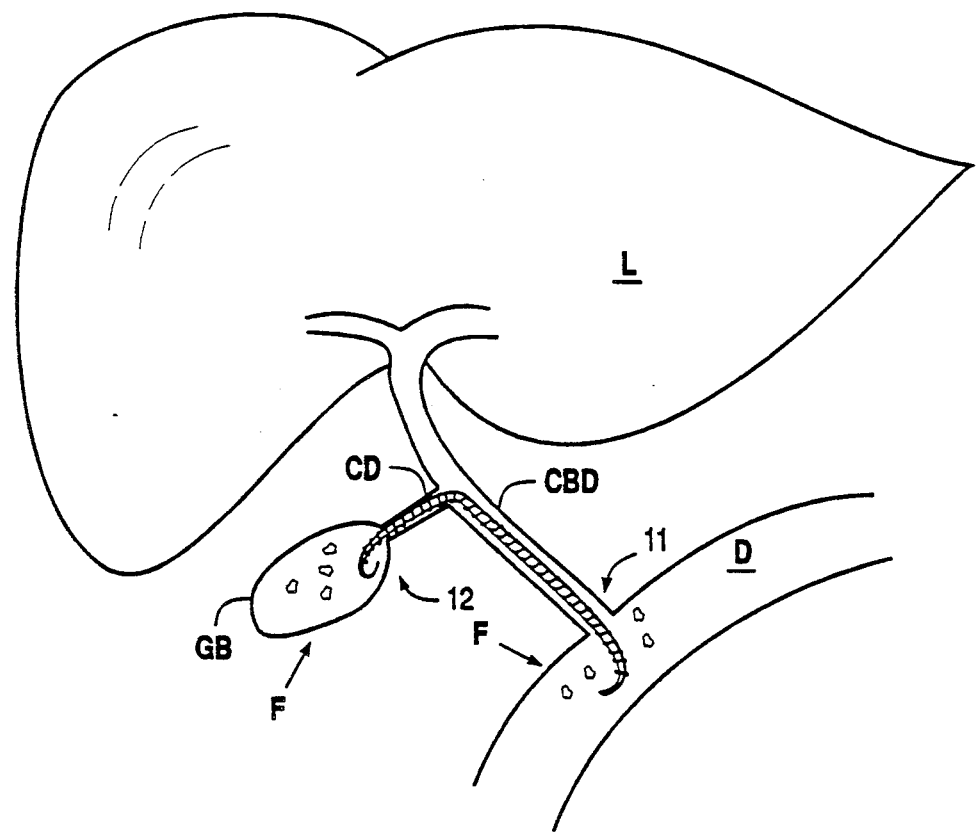

Referring now to FIGS. 10A-B, treatment of stones and their fragments F in a patient's gallbladder GB using the apparatus and method of the present invention will be described. Initially, the patient's gallstones are crushed into fragments F using any of the aforementioned fragmenting techniques, including extracorporeal shockwave lithotripsy.

Next, the stent 1 is introduced into the biliary tract. Specifically, under direct and/or fluoroscopic visualization using conventional endoscopic techniques, the patient's common bile duct CBD is cannulated with the stent 1 before or after lithotripsy. The stent 1 is advanced within the common bile duct CBD so that its proximal J end 12 lies within the hepatic duct HD (common and left or right hepatic ducts) and the distal J end 11 lies within the duodenum D. The convex edge of the helical-like ridge faces towards the liver L (cephalad direction) and the concave edge faces towards the duodenum D (caudal direction).

In FIG. 10B, an alternative placement technique is illustrated. After cannulation of the common bile duct CBD, the stent 1 is advanced into the cystic duct CD so that the proximal J end 12 of the stent lies within the gallbladder GB and the distal J end 11 lies within the duodenum D.

After proper placement, stones and stone fragments F are actively expelled from the patient's gallbladder GB and liver L into the duodenum D by the aforementioned ratcheting, staircase, and/or trapping mechanisms. In addition, pancreatic stones and their fragments will be urged outward in those patients whose pancreatic duct anastomoses with the common bile duct. After resolution of the stones and/or stone fragments, or after a desired period of treatment, the stent is removed and the procedure is terminated.

Those skilled in the art will appreciate certain alternatives which may be practiced within this latter method. The stent 1 may be placed, for example, intraoperatively (e.g., during cholecystectomy). In this manner, the stent 1 is used as an adjuvant to a biliary T-tube. Alternatively, the T-tube may be adapted to include the spaced-apart barrier of the present invention.

While the invention is described in some detail with specific reference to a preferred embodiment and certain alternatives, there is no intent to limit the invention to that particular embodiment or those specific alternatives. Those skilled in the art will appreciate other applications within the scope of the present invention. The stent of the present invention may be adapted, for example, for use in salivary or vascular passages. Therefore, the true scope of the invention is defined not by the foregoing description but by the following claims.

What is claimed is:

1. A stent for placement in a body passage, said stent comprising:
    an elongate flexible body having a proximal end and a distal end;
    means disposed along the elongate body for defining a series of spaced-apart barriers which, when the stent is placed in the body passage, permit the passage of masses from the proximal end towards the distal end but not in an opposite direction; and
    means on the elongate flexible body for self-retaining said body in place within the body passage.

2. The stent of claim 1, wherein the elongate flexible body includes at least one lumen extending from the proximal end to the distal end.

3. The stent of claim 2, wherein said elongate body includes a plurality of radial passageways.

4. The stent of claim 1, wherein said means for defining a series of spaced apart barriers comprises a continuous helical-like ridge.

5. The stent of claim 4, wherein the helical-like ridge includes a smooth, hydrophilic surface.

6. The stent of claim 1, wherein said means for defining a series of spaced apart barriers comprises a non-continuous helical-like ridge.

7. The stent of claim 1, wherein said means for defining a series of spaced apart barriers comprises a plurality of conical ridges.

8. The stent of claim 1, wherein said means for defining a series of spaced apart barriers comprises a plurality of flippers.

9. The stent of claim 1, wherein said means for defining a series of spaced apart barriers comprises a plurality of finger-like projections.

10. The stent of claim 1, wherein said means for defining a series of spaced apart barriers includes a first surface which is substantially convex and a second surface which is substantially concave.

11. The stent of claim 10, wherein the first surface includes a beveled central portion having a plurality of passageways.

12. The stent of claim 1, wherein the self-retaining means includes double-J ends.

13. A method for removing stones from a body passage comprising:
    crushing the stone into fragments;
    placing a stent within the passage, said stent having proximal and distal ends and including a spaced-apart barrier disposed along at least a portion of the stent for transporting the fragments from the proximal end to the distal end; and
    permitting fragments to migrate toward the distal end of the stent in response to natural motion of the passage.

14. The method of claim 13, wherein said barrier includes a continuous helical-like ridge disposed along an outer wall of the stent.

15. The method of claim 14, wherein said continuous helical-like ridge includes a substantially convex surface facing the proximal end and a substantially concave surface facing the distal end.

16. In a stent for maintaining the patency of a body passage, the improvement comprising:
    a series of barriers spaced-apart along substantially the entire length of the stent for transporting masses out of the passage in response to motion of the body passage; and
    radial passages located between at least some of the barriers.

17. The stent of claim 16, wherein said series of barriers comprises a substantially continuous helical-like ridge.

18. A method for removing a stone from a patient's urinary tract comprising:
    crushing the stone into fragments;
    placing a stent within the patient's urinary tract, said stent having proximal and distal ends and including a spaced-apart barrier disposed along at least a portion of the stent for transporting the fragments from the proximal end to the distal end; and
    permitting fragments to migrate out of the urinary tract in response to natural motion of the urinary tract.

19. The method of claim 18, wherein said placing step includes placing the stent within one of the patient's ureters so that a proximate J end of the stent lies within the patient's kidney and a distal J end of the stent lies within the patient's bladder.

20. The method of claim 19, wherein said barrier includes a continuous helical-like ridge disposed along an outer wall of the stent.

21. The method of claim 20, wherein said continuous ridge includes a substantially convex first surface and a substantially concave second surface, said stent being placed so that the first surface faces towards the patient's kidney and the second surface faces towards the patient's bladder.

22. A method for removing a stone from a patient's biliary track comprising:
    crushing the stone into fragments;
    placing a stent within the patient's biliary tract, said stent having proximal and distal ends and including a spaced-apart barrier disposed along at least a portion of the stent for transporting the fragments from the proximal end to the distal end; and
    permitting fragments to migrate out of the biliary tract in response to natural motion of the biliary tract.

23. The method of claim 22, wherein said placing step includes placing the stent within the biliary tract so that a proximal J end of the stent lies within the patient's hepatic duct which opens into the patients liver and a distal J end of the stent within the patient's duodenum.

24. The method of claim 23, wherein said barrier means includes a continuous helical-like ridge disposed along an outer wall of the stent.

25. The method of claim 24, wherein said continuous ridge includes a substantially convex first surface and a substantially concave second surface, said stent being placed so that the first surface faces towards the patient's liver and the second surface faces towards the patient's duodenum.

26. The method of claim 22, wherein said placing step includes placing the stent within the biliary tract so that a proximal J end of the stent lies within the patient's gallbladder and a distal J end of the stent within the patient's duodenum.

* * * * *